United States Patent [19]
Fischer et al.

[11] Patent Number: 5,614,623
[45] Date of Patent: Mar. 25, 1997

[54] DIASTEREOMERS OF 1-(ISOPROPOXYCARBONYLOXY)ETHYL 3-CEPHEM-4-CARBOXYLATE AND PROCESSES FOR THEIR PREPARATION

[75] Inventors: Gerd Fischer, Limburg; Elisabeth Defoβa, Idstein; Uwe Gerlach, Frankfurt am Main; Rolf Hörlein, Frankfurt am Main; Norbert Krass, Frankfurt am Main; Rudolf Lattrell, Königstein/Taunus; Ulrich Stache, Hofheim am Taunus; Theodor Wollmann, Hofheim am Taunus; Dieter Isert, Eschborn, all of Germany

[73] Assignee: Hoechst Aktiengesellschaft, Frankfurt am Main, Germany

[21] Appl. No.: 447,249

[22] Filed: May 22, 1995

Related U.S. Application Data

[62] Division of Ser. No. 940,367, Sep. 3, 1992, Pat. No. 5,461,043.

[30] Foreign Application Priority Data

Sep. 7, 1991 [DE] Germany .......................... 41 29 771.7

[51] Int. Cl.$^6$ .............................................. C07D 501/22
[52] U.S. Cl. ............................................ 540/222; 540/228
[58] Field of Search ......................... 540/222, 228; 514/202

[56] References Cited

U.S. PATENT DOCUMENTS

| | | |
|---|---|---|
| 4,098,888 | 7/1978 | Ochiai et al. . |
| 4,203,899 | 5/1980 | Ochiai et al. . |
| 4,205,180 | 5/1980 | Ochiai et al. . |
| 4,264,595 | 4/1981 | Numata et al. . |
| 4,278,793 | 7/1981 | Dürckheimer et al. . |
| 4,283,396 | 8/1981 | Heymes et al. . |
| 4,298,606 | 11/1981 | Ochiai et al. . |
| 4,355,160 | 10/1982 | Ochiai et al. . |
| 4,409,215 | 10/1983 | Takaya et al. . |
| 4,462,999 | 7/1984 | Takaya et al. . |
| 4,483,855 | 11/1984 | Nakao et al. . |
| 4,486,425 | 12/1984 | Nakao et al. . |
| 4,514,565 | 4/1985 | Ochiai et al. . |
| 4,668,783 | 5/1987 | Ochiai et al. . |
| 4,904,652 | 2/1990 | Takaya et al. . |
| 4,912,212 | 3/1990 | Ochiai et al. . |
| 4,973,684 | 11/1990 | Ochiai et al. . |
| 4,992,431 | 3/1991 | Heymes et al. . |
| 5,026,695 | 6/1991 | Takaya et al. . |
| 5,063,224 | 11/1991 | Misher et al. . |
| 5,100,887 | 3/1992 | Adam et al. . |
| 5,461,043 | 10/1995 | Fischer et al. .......................... 514/202 |

FOREIGN PATENT DOCUMENTS

| | | |
|---|---|---|
| 0034536A2 | 2/1981 | European Pat. Off. . |
| 0034536B1 | 2/1981 | European Pat. Off. . |
| 0029557 | 3/1981 | European Pat. Off. . |
| 0034536A3 | 8/1981 | European Pat. Off. . |
| 0049118A2 | 4/1982 | European Pat. Off. . |
| 0049119 | 4/1982 | European Pat. Off. . |
| 0134420 | 3/1985 | European Pat. Off. . |
| 0379132A2 | 7/1990 | European Pat. Off. . |
| 2556736 | 6/1976 | Germany . |
| 2560398 | 9/1983 | Germany . |
| 60-004190A | 1/1985 | Japan . |
| 60-004189A | 1/1985 | Japan . |
| 2110688 | 6/1983 | United Kingdom . |

OTHER PUBLICATIONS

"Cefpodoxime Proxetil", *Drugs of the Future*, 14(1):73–74 (1989).
"SCE–2174", *Drugs of the Future*, 13(3):231–233 (1988).
"Cefuroxime Axetil", *Drugs of the Future*, 10(2):112–113 (1985).
"β–Lactam Compounds", Chemical Abstract, 102:220658k (1985).

(List continued on next page.)

*Primary Examiner*—Mukund J. Shah
*Assistant Examiner*—Pavanaram K. Sripada
*Attorney, Agent, or Firm*—Finnegan, Henderson, Farabow, Garrett & Dunner, L.L.P.

[57] ABSTRACT

Enterally absorbable diastereomers of 1-(isopropoxycarbonyloxy)ethyl (6R, 7R)-7-[2-(2-aminothiazol-4-yl)-2-(Z)-(methoxyimino)acetamido]-3-(methoxymethyl)-3-cephem-4-carboxylate of the formula I

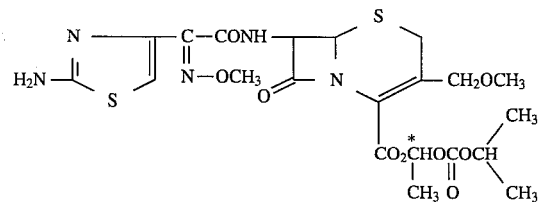

and their physiologically acceptable salts and also diastereomerically pure salts of the compounds of the formula II

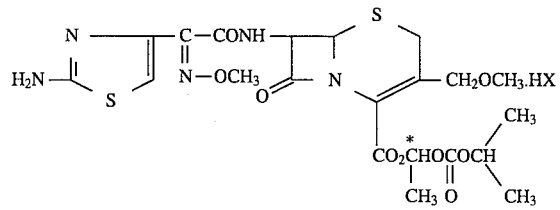

where HX is a mono- or polybasic acid and where X is an inorganic or organic physiologically acceptable anion, and a process for the preparation of these compounds of the formula I or II, which comprises first precipitating the more sparingly soluble diastereomer of the formula IV in the mixing together of 1 equivalent of a solution of the diastereomer mixture of the formula III with 0.2–2 equivalents of a solution of the acid component HY and separating it off by filtration, then precipitating the more readily soluble diastereomer of the formula IV from the filtration solution, it being possible for the acid component HY to be identical or different in the consecutive steps.

11 Claims, No Drawings

OTHER PUBLICATIONS

"Cephalosporin Derivatives", Chemical Abstracts, 102:2206571 (1985).

"Antibiotic Activity of CL 118,673, a New Oral Cephalosporin", N.A. Kuck et al., Recent Advances in Chemotherapy, Proceedings of the 14th Int'l. Congress of Chemotherapy, Antimicrobial Section 2, pp. 1137–1138, (1985).

"Improved Synthesis of an Ester-type Prodrug, 1-Acetoxyethyl 7-[(Z)-2-(2-Aminothiazol-4-yl)-2-Hydroxyiminoacetamido]-3-[(Z)-1-Propenyl]-3-Cephem-4-Carboxylate (BMY-28271)", Hajime Kamachi et al., The Journal of Antibiotics, vol. XLIII(12):1564–1572 (1990).

"Orally Active 1-(Cyclohexyloxycarbonyloxy)alkyl Ester Prodrugs of Cefotiam", Tatsuo Nishimura et al., The Journal of Antibiotics, vol. XL(1):81–90 (1987).

DIASTEREOMERS OF 1-(ISOPROPOXYCARBONYLOXY)ETHYL 3-CEPHEM-4-CARBOXYLATE AND PROCESSES FOR THEIR PREPARATION

This is a division of application Ser. No. 07/940,367, filed Sep. 3, 1992, now U.S. Pat. No. 5,461,043.

The invention relates to enterally absorbable diastereomers of 1-(isopropoxycarbonyloxy)ethyl (6R, 7R)-7-[2-(2-aminothiazol-4-yl)-2-(Z)-(methoxyimino)acetamido]-3-(methoxymethyl)-3-cephem-4-carboxylate of the formula I and their physiologically acceptable salts

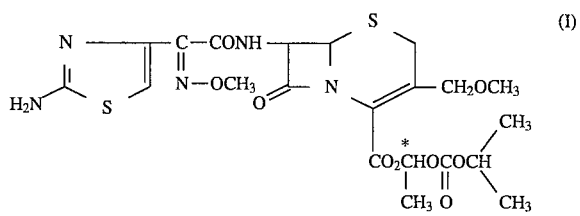

and to processes for their preparation.

In U.S. Pat. No. 4,486,425, esters of (6R,7R)-7-[2-(2-aminothiazol-4-yl)-2-(Z)-(methoxyimino)acetamido]3-(methoxymethyl)-3-cephem-4-carboxylic acid are described. Of these, the ester of the formula I is of particular interest, since it is readily enterally absorbed in various animal species and in man and, after absorption, is rapidly and completely cleaved to give the antibiotically active cephalosporin having a free carboxyl group by enzymes endogenous to the body. This compound is known under the name cefpodoxime proxetil (Drugs of the Future 14, 73 (1989)).

The ester of the formula I has two asymmetric carbon atoms, in each case of (R)-configuration, in the 6- and 7-position of the cephem structure and an asymmetric carbon atom in the 1-position of the ethyloxy ester group —O—CH(CH$_3$)—O—. The compounds described in U.S. Pat. No. 4,486,425 exist as mixtures of the diastereomers with respect to the asymmetric carbon atom of the 1-ethyloxy ester group —O—CH(CH$_3$)—O—. Comparable mixtures of diastereomers also exist, for example, in the case of cefotiam hexetil (Drugs of the Future 13, 230 (1988)), cefuroxime axetil (Drugs of the Future 10, 112 (1985)), baccefuzonam (N.A. Kuck et al., Proc. 14th Int. Congr. Chemother. 2, 1137 (1985)) and BMY28271 (The Journal of Antibiotics 43, 1564 (1990)).

According to the experiments to date on the mechanism of the enteral absorption of cephem prodrug esters of this type, the configuration in the 1-position of the ethyl ester group —O—CH(CH$_3$)—O— has no effect on the level of enteral absorption. It was possible to show this experimentally, for example, for the diastereomers of cefotiam hexetil (T. Nishimura et al., The Journal of Antibiotics 40, 81–90 (1987)).

In the case of cefotiam hexetil, the two diastereomers were chromatographically separated. However, this route is associated with high losses and is not generally practicable, since the physical properties of the two diastereomers, such as, for example, in the case of cefpodoxime proxetil, are too similar to enable a chromatographic separation. In addition, both diastereomers and the diastereomer mixture are unstable under the conditions of column chromatography.

The two separate diastereomers of cefpodoxime proxetil have therefore not been described hitherto. Also, no preparative processes have been disclosed specifically to prepare the two diastereomers of cephalosporin ester prodrugs which, like cefpodoxime proxetil, are derived from the 1-ethyloxy ester radical —O—CH(CH$_3$)—O—.

It was therefore surprising that the separate diastereomers of the formula I exhibit distinct differences in enteral absorption, such that the more absorbable diastereomer exhibited a higher bioavailability than the diastereomer mixture of cefpodoxime proxetil.

The present invention therefore relates to diastereomerically pure compounds of the formula I in which the group =N—OCH$_3$ is in the syn-position. The preferred diastereomer is the more polar of the two diastereomers, which has the higher bioavailability.

The present invention also relates to diastereomerically pure salts of the formula II

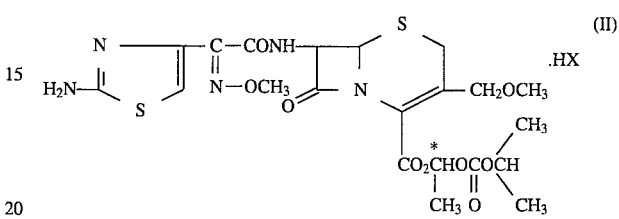

where HX is a mono- or polybasic acid and where X can be an inorganic or organic physiologically acceptable anion.

As an inorganic acid, HX is, for example, the stoichiometric amount of HCl, HBr, HI, HBF$_4$, HNO$_3$, HClO$_4$, H$_2$SO$_4$ or H$_3$PO$_4$. As an organic acid, HX is aliphatic or aromatic sulfonic acids. The inorganic acids HCl, HBr and H$_2$SO$_4$ and the organic acids methanesulfonic acid, ethanesulfonic acid, benzenesulfonic acid, p-toluenesulfonic acid and 4-ethylbenzenesulfonic acid are particularly preferred.

This invention furthermore relates to a process for the preparation of diasteroemerically pure compounds of the formula I, which comprises preparing an intermediate of the formula III

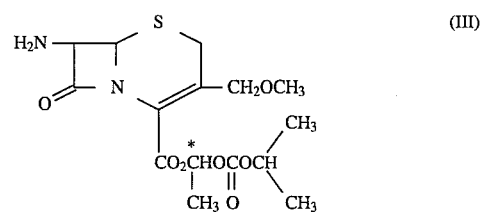

or of the formula IV

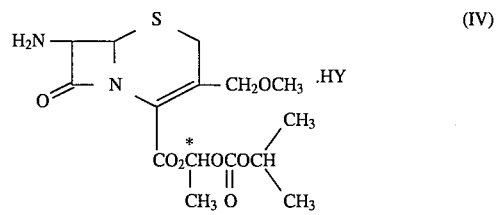

in diastereomerically pure form and converting it into the pure diastereomers of the formula I or of the formula II.

The pure diastereomers of the formula I thus obtained are converted into the salts of the formula II by methods which are known per se, such as have been described, for example, for analogous compounds.

The compound of the formula III or its salts of the formula IV are prepared by processes known per se, which have been described, for example, in Patent Application JP 60,004, 190A, as a mixture of diastereomers.

The diastereomers can be separated by fractional crystallization of salts of the formula IV. In the formula IV, HY is a mono- or polybasic acid, where Y can be inorganic or organic anion.

As an inorganic acid, HY is, for example, HCl, HBr, HI, HF, HNO$_3$, HClO$_4$, HSCN, H$_2$SO$_4$ or H$_3$PO$_4$. As an organic acid, HY is aliphatic or aromatic sulfonic acids, carboxylic acids or phosphoric acids. Thus, for example, the following organic acids can be employed: benzenesulfonic acid, p-toluenesulfonic acid, 4-ethylbenzenesulfonic acid, 4-chlorobenzenesulfonic acid, 4-bromobenzenesulfonic acid, 2-mesitylenesulfonic acid, 4-biphenylsulfonic acid, naphthalene-1,5-disulfonic acid, methanesulfonic acid, ethanesulfonic acid, dodecylsulfonic acid, camphorsulfonic acid and oxalic acid.

The following must be regarded as preferred acid components: HCl, HBr, benzenesulfonic acid, p-toluenesulfonic acid, 4-ethylbenzenesulfonic acid and 4-biphenylsulfonic acid.

The salt of the formula IV is prepared by mixing together a solution of the diastereomer mixture of the formula III and a solution of the acid component HY. The organic solvents employed can be, for example, alcohols, ethers, esters, alcohols, ketones, nitriles, chlorinated hydrocarbons and hydrocarbons and also their mixtures. Preferred solvents are, for example, benzene, toluene, ethyl acetate, butyl acetate, methanol, ethanol, n-propanol, isopropanol, tert-butanol, diisopropyl ether, acetone, acetonitrile and dichloromethane and mixtures thereof.

As the solvents for inorganic acids, water can additionally be employed if the organic solvent is miscible with water. Solutions of HCl and HBr in organic solvents can be produced, for example, by passing in hydrogen chloride or hydrogen bromide gas. Solutions of HCl and HBr in organic solvents can also be produced from acetyl halides, phosphorus halides and phosphorus oxyhalides and an alcohol (halogen=Cl, Br).

An important factor for the separation of the diastereomers is the ratio of the base of the formula III to the acid component. For one equivalent of the diastereomer mixture of the formula III, 0.2–2.0, preferably 0.4–1.5, equivalents of acid components should be employed.

For the process, it is essential that the precipitation of the pure diastereomers of the formula IV is effected in two consecutive partial steps. Thus, for example, by mixing together a solution of the diastereomer mixture of the formula III with a solution of the acid component HY, first the more sparingly soluble diasteromer of the formula IV is precipitated and separated off by filtration, and then the more readily soluble diastereomer of the formula IV is precipitated from the filtration solution. In the consecutive partial steps, the acid component HY can be identical or different, any desired sequence of the addition of different acid components HY being possible. Thus, for example, the more polar diastereomer of the formula IV or the less polar diastereomer of the formula IV can be precipitated first as the more sparingly soluble salt by suitable choice of the acid component HY.

By means of the choice of the acid component, both diastereomers of the formula IV can thus be obtained in pure form. Thus, for example, when using hydrogen chloride or hydrogen bromide, the more polar diastereomer is preferably obtained first, while the use of benzenesulfonic acid, 4-ethylbenzenesulfonic acid, biphenylsulfonic acid or p-toluenesulfonic acid preferably yields the less polar diastereomer.

The salts obtained after filtration are further purified, if necessary, by crystallization. To do this, the solvents described above and their mixtures are employed. The choice of the optimum solvent depends on the acid component used. Thus, for example, for the p-toluenesulfonic acid salt and for the hydrochloride, methanol, ethanol, n-propanol, isopropanol, acetonitrile, ethyl acetate and dichloromethane are particularly suitable.

The acid component is added at about −10° C. to +50° C., preferably at +10° C. to +30° C. Depending on the acid component and the solvent, the mixture is further stirred to complete the precipitation for up to about 10 hours. If necessary, the mixture must be cooled to temperatures between room temperature and about −78° C. to complete the precipitation.

Alternatively, diastereomer mixtures of the formula III can also be obtained starting from compounds of the formula V

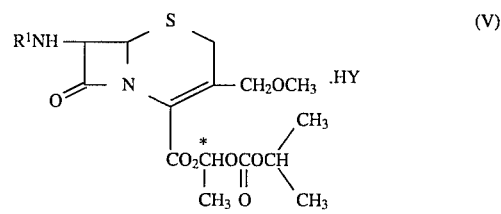

The group $R^1$ is in this case an amino-protective group customary in peptide chemistry, such as, for example, the formyl group, the tert-butoxycarbonyl group, the chloroacetyl group, the phenoxyacetyl group, the phenylacetyl group, the alkoxycarbonyl group, the benzyloxycarbonyl group and the 4-nitrobenzyloxycarbonyl group.

The protective groups are removed by methods known per se. Thus, the formyl group and the tert-butoxycarbonyl group are removed, for example, with acid. The phenoxyacetyl group and the phenylacetyl group can be removed, for example, with phosphorus pentachloride or enzymatically with penicillin acylases. In the case of the allyloxycarbonyl group, removal can be carried out with $Pd[P(C_6H_5)_3]$. The benzyloxycarbonyl group and the 4-nitrobenzyloxycarbonyl group can be removed by hydrogenolysis.

In the case of the removal of the phenoxyacetyl group or the phenylacetyl group with phosphorus pentachloride, the more polar diastereomer is obtained as a hydrochloride even without addition of hydrogen chloride. Unremoved phosphoric acid ester chlorides, which slowly liberate hydrogen chloride, serve as a source of hydrogen chloride in the work-up.

Starting from compounds of the formula V, diastereomerically pure compounds of the formula III or of the formula IV can be obtained by first carrying out the separation of the diastereomers, removing the protective group and optionally precipitating the diastereomer mixture of the formula IV with an excess of the acid component HY. The separation of the diastereomers of the formula V can be carried out by crystallization or chromatography, the exact conditions depending on the protective group $R^1$. If, for example, $R^1$ is the phenoxyacetyl group, the diastereomers can be separated by chromatography on silica gel using an organic solvent mixture.

Starting from the diastereomerically pure salts of the formula IV, the diastereomerically pure bases of the formula III are prepared by methods known per se and these are converted, as described, for example, for the diastereomer mixture in the Patent Application JP60,004,189A, into the pure diastereomers of the formula I.

To do this, the diastereomerically pure compounds of the formula III can be reacted, for example, with a compound of the formula VI

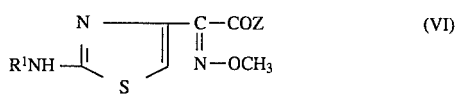

where $R^1$ is hydrogen or has the meaning described above for compounds of the formula V, and Z is an activating group customary in beta-lactam chemistry, such as, for example, chloride, p-toluenesulfonyl, 1-benzotriazolyloxy or mercaptobenzothiazolyl.

The unforeseeable, advantageous properties of the present invention lie in an increased enteral absorption of the more polar diastereomer of the formula I, as is shown in Table 1.

TABLE 1

| Diastereomer composition | Recovery rate |
| --- | --- |
| Diastereomer A (Example 7) | 25% |
| Diastereomer B (Example 8) | 45% |

Table 1 shows the recovery rate (0–24 h) of (6R,7R)-7-[2-(2-aminothiazol-4-yl)-2-(Z)-(methoxyimino)-acetamido]-3-(methoxymethyl)-3-cephem-4-carboxylic acid in the urine of dogs after oral administration of the diastereomeric prodrug ester (dose: 10 mg/kg based on the biologically active substance).

The compounds of the formula I according to the invention are orally administered in the form of customary pharmaceutical preparations, such as, for example, capsules, tablets, powders, syrups or suspensions. The dose depends on the age, the symptoms and the body weight of the patient and on the duration of the treatment. However, it is as a rule between about 0.2 g and about 5 g daily, preferably between about 0.5 g and about 3 g daily. The compounds are preferably administered in divided doses, for example 2 to 4 times daily, it being possible for the individual dose to contain, for example, between 50 and 500 mg of active substance.

The oral preparations can contain the customary excipients and/or diluents. Thus, for example, for capsules or tablets binders, such as, for example, gelatine, sorbitol, polyvinylpyrrolidone or carboxymethylcellulose, diluents, such as, for example, lactose, sugar, starch, calcium phosphates or polyethylene glycol, lubricants, such as, for example, talc or magnesium stearate, are possible. For liquid preparations, for example aqueous or oily suspensions, syrups or similar known preparation forms are suitable.

The following exemplary embodiments of diastereomerically pure compounds of the formula I and formula II which can be prepared according to the invention are used to illustrate the invention further, but do not restrict it thereto.

EXPERIMENTAL SECTION

Example 1

1-(Isopropoxycarbonyloxy)ethyl (6R, 7R)-7-amino-3-methoxymethyl-3-cephem-4-carboxylate p-toluenesulfonate (diastereomer mixture)

1.22 g (5 mmol) of (6R,7R)-7-amino-3-methoxymethyl-3-cephem-4-carboxylic acid were suspended in 15 ml of dichloromethane under an argon atmosphere and brought into solution by addition of 0.75 ml (5 mmol) of DBU. At 0° C., 1.43 g (5.5 mmol) of 1-iodoethyl-isopropylcarbonate (The Journal of Antibiotics 40, 370 (1987)) were added, and the mixture was stirred for a further 40 minutes at 0° C. and for 30 minutes at 20° C. and diluted for working up with 50 ml of ethyl acetate. The mixture was washed with satd. aq. NaHCO$_3$ and NaCl solution, and dried with MgSO$_4$, and the organic phase was concentrated in vacuo. The crude product was taken up in 5 ml of ethyl acetate and a solution of 1.0 g (5.3 mmol) of p-toluenesulfonic acid monohydrate in 5 ml of ethyl acetate was added at 20° C. 10 ml of diisopropyl ether were additionally added, the mixture was cooled to 0° C. and the precipitated product was filtered off with suction.

Yield: 1.93 g (71% of theory). $^1$H NMR (DMSO-d$_6$, 270 MHz): d=1.25 (m, 6H, C(CH$_3$)$_2$); 1.50 (d, 3H, CH—CH$_3$); 2.30 (s, 3H, aryl—CH$_3$); 3.23 (s, 3H, CH$_2$OCH$_3$); 3.70 (2H, m, S—CH$_2$); 4.21 (m, CH$_2$OCH$_3$); 4.81 (m, 1H, O—CH(CH$_3$)$_2$); 5.25 (m, 2H, H-6 and H-7); 6.81 and 6.85 (2xq, 1H, O—CH(CH$_3$)—O); 7.11 and 7.48 (2xd, 4H, aryl—H) 9.05 (br s, 2H, NH$_2$).

TLC (toluene/ethyl acetate 1+1): R$_f$=0.34 (diastereomer A) and 0.26 (diastereomer B).

HPLC: C18 Nukleosil 7 μm; water (+0.1% NH$_4$OAc)+(methanol/water 80:20 (+0.1% NH$_4$OAc)) 45:55, 1 ml/min= 10.8 min. (diastereomer A), 9.1 min. (diastereomer B).

Example 2

1-(Isopropoxycarbonyloxy)ethyl (6R,7R)-7-amino-3-methoxy-methyl-3-cephem-4-carboxylate (diastereomer mixture)

2.53 g (4.6 mmol) of diastereomer mixture from Example 1 were taken up in a mixture of ethyl acetate and 5% strength aq. NaHCO$_3$ solution and stirred for 5 min. The phases were separated, and the organic phase was washed with satd. aq. NaCl solution, dried with MgSO$_4$ and concentrated in vacuo.

Yield: 1.74 g (100% of theory).

Example 3

I) 1-(Isopropoxycarbonyloxy)ethyl (6R,7R)-7-amino-3-methoxymethyl-3-cephem-4-carboxylate p-toluenesulfonate (diastereomer A)

1.74 g (4.63 mmol) of diastereomer mixture from Example 2 were taken up in 4 ml of ethyl acetate and a solution of 0.44 g (2.32 mmol) of p-toluenesulfonic acid monohydrate in 3 ml of ethyl acetate was added. 3 ml of diisopropyl ether were additionally added and the precipitated product was filtered off with suction. The filtration solution was reused as described in Example 3 (II).

Yield: 0.904 g (36% of theory) of diastereomer A (p-toluenesulfonate).

$^1$H NMR (DMSO-d$_5$, 270 MHz): d=1.25 (m, 6H, C(CH$_3$)$_2$); 1.50 (d, 3H, CH—CH$_3$); 2.30 (s, 3H, aryl—CH$_3$); 3.23 (s, 3H, CH$_2$OCH$_3$); 3.69 (2H, ABq, S—CH$_2$); 4.21 (m, CH$_2$OCH$_3$); 4.79 (m, 1H, O—CH(CH$_3$)$_2$); 5.25 (m, 2H, H-6 and H-7); 6.81 (q, 1H, O—CH(CH$_3$)—O); 7.11 and 7.48 (2xd, 4H, aryl—H); 8.9 (br s, 2H, NH$_2$).

TLC (toluene/ethyl acetate 1+1): R$_f$=0.34.

HPLC: C18 Nukleosil 7 μm; water (+0.1% NH$_4$OAc)+(methanol/water 80:20 (+0.1% NH$_4$OAc)) 45:55, 1 ml/min= 10.8 min. (diastereomer A).

II) 1-(Isopropoxycarbonyloxy)ethyl (6R,7R)-7-amino-3-methoxymethyl-3-cephem-4-carboxylate p-toluenesulfonate (diastereomer B)

The filtration solution obtained from Example 3 (I) was treated with a solution of 0.44 g (2.32 mmol) of p-toluenesulfonic acid monohydrate in 3 ml of ethyl acetate and the precipitated product was filtered off with suction.

Yield: 0.534 g (21% of theory) of diastereomer B (p-toluenesulfonate).

$^1$H NMR (DMSO-d$_6$, 270 MHz): d=1.25 (m, 6H, C(CH$_3$)$_2$); 1.50 (d, 3H, CH—CH$_3$); 2.30 (s, 3H, aryl—CH$_3$); 3.23 (s, 3H, CH$_2$OCH$_3$); 3.69 (2H, m, S—CH$_2$); 4.21 (m, CH$_2$OCH$_3$); 4.79 (m, 1H, O—CH(CH$_3$)$_2$); 5.25 (m, 2H, H-6 and H-7); 6.84 (q, 1H, O—CH(CH$_3$)—O); 7.11 and 7.48 (2xd, 4H, aryl—H); 8.9 (br s, 2H, NH$_2$).

TLC (toluene/ethyl acetate 1+1): $R_f$=0.26.

HPLC: C18 Nukleosil 7 μm; water (+0.1% NH$_4$OAc)+ (methanol/water 80:20 (+0.1% NH$_4$OAc)) 45:55, 1 ml/min= 9.1 min. (diastereomer B).

Example 4

I) 1-(Isopropoxycarbonyloxy)ethyl(6R,7R)-7-amino-3-methoxymethyl-3-cephem-4-carboxylate hydrochloride (diastereomer B)

1.71 g (4.57 mmol) of diastereomer mixture from Example 2 were taken up in 4 ml of ethyl acetate and 0.914 ml (2.28 mmol) of 2.45M isopropanolic hydrochloric acid were added. The resulting precipitate was filtered off with suction and the filtration solution was reused as described in Example 4 (II).

Yield: 0.628 g (41% of theory) of diastereomer B (hydrochloride).

$^1$H NMR (DMSO-d$_6$, 270 MHz): d=1.25 (m, 6H, C(C$\underline{H}_3$)$_2$); 1.48 (d, 3H, C$\underline{H}$—CH$_3$); 3.23 (s, 3H, CH$_2$OC$\underline{H}_3$); 3.68 (2H, m, S—C$\underline{H}_2$); 4.21 (s, C$\underline{H}_2$OCH$_3$); 4.81 (m, 1H, O—C$\underline{H}$(CH$_3$)$_2$); 5.21 (q, 2H, H-6 and H-7); 6.85 (q, 1H, O—C$\underline{H}$(CH$_3$)—O); 9.2 (br s, 2H, N$\underline{H}_2$).

TLC (toluene/ethyl acetate 1+1): $R_f$=0.26.

HPLC: C18 Nukleosil 7 μm; water (+0.1% NH$_4$OAc)+ (methanol/water 80:20 (+0.1% NH$_4$OAc)) 45:55, 1 ml/min= 9.1 min. (diastereomer B).

II) 1-(Isopropoxycarbonyloxy)ethyl (6R, 7R)-7-amino-3-methoxymethyl-3-cephem-4-carboxylate p-toluenesulfonate (diastereomer A)

The filtration solution obtained from Example 4 (I) was treated with a solution of 0.573 g (3.0 mmol) of p-toluenesulfonic acid monohydrate in 3 ml of ethyl acetate and the precipitated product was filtered off with suction.

Yield: 0.808 g (38% of theory) of diastereomer A (p-toluenesulfonate), identical with the product from Example 3 (I).

Example 5

1-(Isopropoxycarbonyloxy)ethyl (6R, 7R)-7-amino-3-methoxymethyl-3-cephem-4-carboxylate (diastereomer A)

4.83 g (8.8 mmol) of diastereomer A from Example 4 (II) were taken up in a mixture of 80 ml of ethyl acetate and 153 ml of water using 0.96 g (11.45 mmol) of NaHCO$_3$ and stirred for 5 min. The phases were separated, and the organic phase was washed with satd. aq. NaCl solution, dried with MgSO$_4$ and concentrated in vacuo.

Yield: 3.29 g (100% of theory).

Example 6

1-(Isopropoxycarbonyloxy)ethyl (6R,7R)-7-amino-3-methoxymethyl-3-cephem-4-carboxylate (diastereomer B)

4.99 g (12.0 mmol) of diastereomer B from Example 4 (I) were taken up in a mixture of 110 ml of ethyl acetate and 219 ml of water using 1.36 g (16.28 mmol) of NaHCO$_3$ and stirred for 5 min. The phases were separated, and the organic phase was washed with satd. aq. NaCl solution, dried with MgSO$_4$ and concentrated in vacuo.

Yield: 4.49 g (100% of theory).

Example 7

1-(Isopropoxycarbonyloxy)ethyl (6R,7R)-7-[2-(2-aminothiazol-4-yl)-2-(Z)-[methoxyimino)acetamido]-3-methoxymethyl-3-cephem-4-carboxylate (diastereomer A)

3.29 g (8.8 mmol) of diastereomer A from Example 5 were dissolved in 22 ml of dry dichloromethane under an argon atmosphere and 3.19 g (9.11 mmol) of 2-(2-aminothiazol-4-yl)-2(Z)-(methoxyimino)mercaptobenzothiazolyl acetate were added. The suspension was stirred for a further hour at 20° C., then diluted with 200 ml of ethyl acetate and extracted twice with water, the extract was dried with MgSO$_4$ and the solvent was stripped off in vacuo. The residue was purified by column chromatography ( SiO$_2$, toluene/ethyl acetate).

Yield: 1.1 g (22% of theory) of diastereomer A.

$^1$H NMR (DMSO-d$_6$, 270 MHz): d=1.23 (dd, 6H, C(C$\underline{H}_3$)$_2$); 1.49 (d, 3H, CH—C$\underline{H}_3$); 3.21 (s, 3H, CH$_2$OC$\underline{H}_3$); 3.48 (2H, ABq, S—C$\underline{H}_2$); 3.83 (s, 3H, N—OC$\underline{H}_3$); 4.14 (s, C$\underline{H}_2$OCH$_3$); 4.80 (m, 1H, O—C$\underline{H}$(CH$_3$)$_2$); 5.21 (d, 1H, H-6); 5.82 (dd, 1H, H-7); 6.72 (s, 1H, thiazole-H); 6.80 (q, 1H, O—C$\underline{H}$(CH$_3$)—O); 7.2 (br s, 2H, N$\underline{H}_2$); 9.59 (d, 1H, CON$\underline{H}$).

HPLC: C18 Nukleosil 7 μm; water+1.2-dimethoxyethane (+EDTA 10 mg/l, +0.2% N-methylmorpholine, +HClO$_4$, pH 3.34) 68:32; 1.5 ml/min; 12.6 min. (diastereomer A).

Example 8

1-(Isopropoxycarbonyloxy)ethyl (6R, 7R)-7-[2-(2-aminothiazol-4-yl)-2-(Z)-(methoxyimino)acetamido]-3-methoxy-methyl-3-cephem-4-carboxylate (diastereomer B)

4.49 g (12.0 mmol) of diastereomer B from Example 6 were dissolved in 30 ml of dry dichloromethane under an argon atmosphere and 4.39 g (12.42 mmol) of 2-(2-aminothiazol-4-yl)-2(Z)-(methoxyimino)mercaptobenzothiazolyl acetate were added. The suspension was stirred for a further hour at 20° C., then diluted with 200 ml of ethyl acetate and extracted twice with water, the extract was dried with MgSO$_4$ and the solvent was stripped off in vacuo. The residue was purified by column chromatography (SiO$_2$, toluene/ethyl acetate).

Yield: 4.6 g (69% of theory) of diastereomer B.

$^1$H NMR (DMSO-d$_6$, 270 MHz): d=1.25 (dd, 6H, C(C$\underline{H}_3$)$_2$); 1.50 (d, 3H, CH—C$\underline{H}_3$); 3.21 (s, 3H, CH$_2$OC$\underline{H}_3$); 3.53 (2H, ABq, S—CH$_2$); 3.85 (s, 3H, N—OC$\underline{H}_3$); 4.14 (s, C$\underline{H}_2$OCH$_3$); 4.81 (m, 1H, O—C$\underline{H}$(CH$_3$)$_2$); 5.19 (d, 1H, H-6); 5.81 (dd, 1H, H-7); 6.72 (s, 1H, thiazole-H); 6.83 (q, 1H, O—C$\underline{H}$(CH$_3$)—O); 7.2 (br s, 2H, N$\underline{H}_2$); 9.59 (d, 1H, CON$\underline{H}$).

HPLC: C18 Nukleosil 7 μm; water+1.2-dimethoxyethane (+EDTA 10 mg/l, +0.2% N-methylmorpholine, +HClO$_4$, pH 3.34) 68:32; 1.5 ml/min; 9.7 min. (diastereomer B).

Example 9

1-(Isopropoxycarbonyloxy)ethyl (6R, 7R)-7-[2-(2-aminothiazol-4-yl)-2-(Z)-(methoxyimino)acetamido]-3-methoxymethyl-3-cephem-4-carboxylate (diastereomer mixture, Cefpodoxime Proxetil)

4.26 g (17.5 mmol) of (6R,7R)-7-amino-3-methoxymethyl-3-cephem-4-carboxylic acid were suspended in 40 ml of dichloromethane under an argon atmosphere and brought into solution by addition of 2.65 g (17.5 mmol) of DBU. At 0° C., 4.96 g (19.2 mmol) of 1-iodoethyl-isopropyl-carbonate (The Journal of Antibiotics 40, 370 (1987)) were added, and the mixture was stirred for a further 60 minutes at 0° C. and for 20 minutes at 20° C. 6.4 g (18.3 mmol) of 2-(2-aminothiazol-4-yl)-2(Z)-(methoxyimino)mercaptobenzothiazolyl acetate were then added. The suspension was stirred for a further 2 hours at 20° C., then diluted with 200 ml of ethyl acetate and extracted twice with water, the extract was dried with MgSO$_4$ and the solvent was stripped off in vacuo. The residue was purified by column chromatography (SiO$_2$, toluene/ethyl acetate).

Yield: 3.42 g (35% of theory) of diastereomer mixture A+B.

$^1$H NMR (DMSO-d$_6$, 270 MHz): d=1.25 (m, 6H, C(C$\underline{H}_3$)$_2$); 1.49 (m, 3H, CH—C$\underline{H}_3$); 3.21 (s, 3H, CH$_2$OC$\underline{H}_3$); 3.54 (2H, ABq, S—C$\underline{H}_2$); 3.85 (s, 3H, N—OC$\underline{H}_3$); 4.14 (s, C$\underline{H}_2$OCH$_3$); 4.8 (m, 1H, O—C$\underline{H}$(CH$_3$)$_2$); 5.21 (m, 1H, H-6); 5.82 (m, 1H, H-7); 6.72 (s, 1H, thiazole-H); 6.80 and 6.83 (2xq, 1H, O—($\underline{H}$(CH$_3$)—O); 7.2 (br s, 2H, N$\underline{H}_2$); 9.6 (m, 1H, CON$\underline{H}$).

HPLC: C18 Nukleosil 7 μm; water+1.2-dimethoxyethane (+EDTA 10 mg/l, +0.2% N-methylmorpholine, +HClO$_4$, pH 3.34) 68:32; 1.5 ml/min; 12.6 min. (diastereomer A), 9.7 min. (diastereomer B).

We claim:

1. A process for the preparation of a diastereomerically pure compound of the formula I

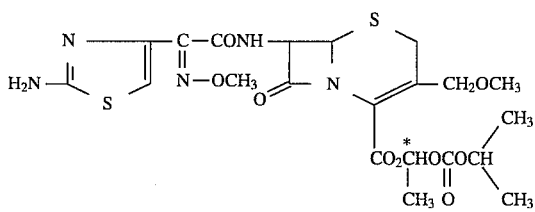

or a diastereomerically pure salt thereof of the formula II

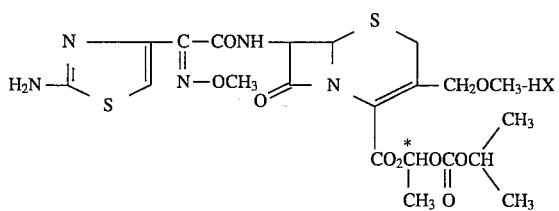

where HX is a mono- or polybasic acid and X is an inorganic or organic physiologically acceptable anion, which comprises preparing a diastereomer mixture of intermediates of the formula III

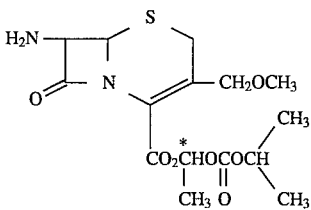

or of the formula IV

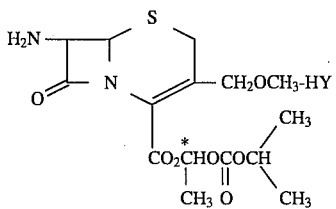

in which HY is a mono- or polybasic acid, where Y is an inorganic or organic anion, in diastereomerically pure form and converting the intermediate into the pure diastereomers of the formula I or of the formula II.

2. The process of claim 1, further comprising mixing 1 equivalent of a solution of the diastereomer mixture of the formula III with 0.2–2 equivalents of a solution of the acid component HY to precipitate the more sparingly soluble diastereomer of the formula IV, separating said more sparingly soluble diastereomer by filtration, and precipitating the more readily soluble diastereomer of the formula IV from the filtration solution with 0.2–2 equivalents of a solution of the acid component HY.

3. The process of claim 2, wherein the amount of the acid component ranges from 0.4–1.5 equivalents.

4. The process of claim 2, wherein the acid component of said mixing and precipitating steps is identical or different.

5. The process of claim 2, wherein the acid component is chosen such that the more polar diastereomer of formula III precipitates as the more sparingly soluble diastereomer of formula IV.

6. The process of claim 5, wherein the acid component is selected from hydrogen chloride or hydrogen bromide.

7. The process of claim 2, wherein the acid component is chosen such that the less polar diastereomer of formula III precipitates as the more sparingly soluble diastereomer of formula IV.

8. The process of claim 7, wherein the acid component is selected from benzenesulfonic acid, 4-ethylbenzenesulfonic acid, biphenylsulfonic acid, or p-toluenesulfonic acid.

9. The process of claim 2, further comprising purifying the more sparingly soluble diastereomer or the more readily soluble diastereomer by crystallization.

10. The process of claim 1, wherein the diastereomerically pure intermediates of formulae III or IV are converted into the pure diastereomers of formula I or II by reacting the intermediates of formula III or IV with a compound of the formula VI having the following structural formula:

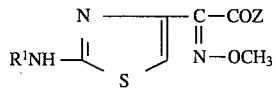

wherein R$^1$ denotes hydrogen and Z represents an activating group customary in beta-lactam chemistry.

11. The process of claim 2, wherein Z represents chloride, p-toluenesulfonyl, 1-benzotriazolyloxy, or mercaptobenzothiazolyl.

* * * * *

UNITED STATES PATENT AND TRADEMARK OFFICE
CERTIFICATE OF CORRECTION

PATENT NO. : 5,614,623           Page 1 of 2
DATED      : March 25, 1997
INVENTOR(S) : Gerd Fishcher et al.

It is certified that error appears in the above-indentified patent and that said Letters Patent is hereby corrected as shown below:

On the Title page, Item [57], in the Abstract delete formula II " 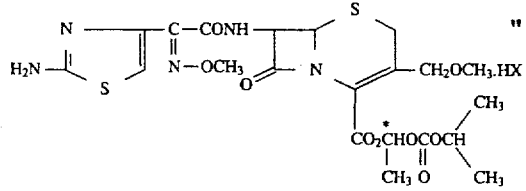 "

and insert -- 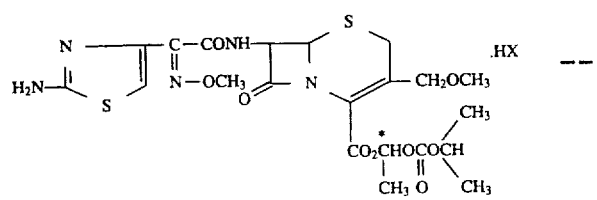 --

Claim 1, column 9, lines 29-36, delete formula II 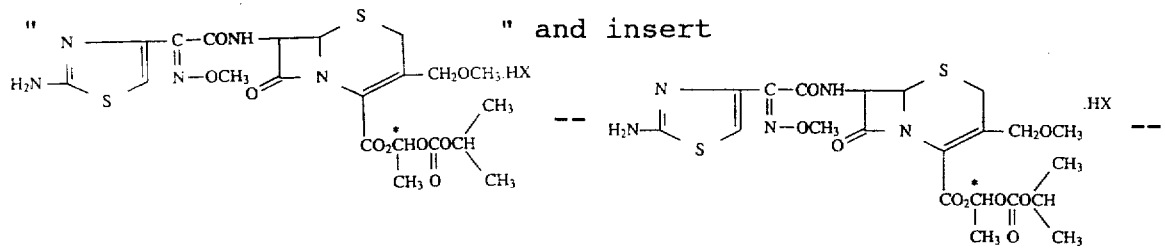

UNITED STATES PATENT AND TRADEMARK OFFICE
CERTIFICATE OF CORRECTION

PATENT NO. : 5,614,623
DATED : March 25, 1997
INVENTOR(S) : Gerd Fishcher et al.

It is certified that error appears in the above-identified patent and that said Letters Patent is hereby corrected as shown below:

Claim 1, column 9, lines 52-60, delete formula IV

" 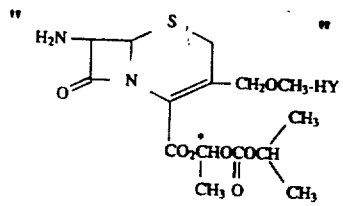 " and insert -- 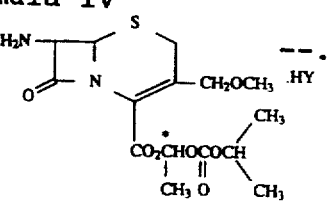 --.

Signed and Sealed this

Twenty-eighth Day of April, 1998

*Attest:*

BRUCE LEHMAN

*Attesting Officer*  *Commissioner of Patents and Trademarks*